United States Patent [19]
Bernstein

[11] Patent Number: 5,169,789
[45] Date of Patent: Dec. 8, 1992

[54] DEVICE AND METHOD FOR SELF CONTAINED SOLID PHASE IMMUNODIFFUSION ASSAY

[75] Inventor: David Bernstein, Sykesville, Md.

[73] Assignee: New Horizons Diagnostics Corporation, Columbia, Md.

[21] Appl. No.: 818,439

[22] Filed: Dec. 27, 1991

Related U.S. Application Data

[63] Continuation of Ser. No. 262,503, filed as PCT/US87/03169, Dec. 1, 1987, abandoned, which is a continuation-in-part of Ser. No. 938,003, Dec. 3, 1986, Pat. No. 4,770,853.

[51] Int. Cl.⁵ .......................................... G01N 33/545
[52] U.S. Cl. ........................................ 436/501; 422/56; 422/57; 422/61; 436/524; 436/528; 436/531
[58] Field of Search ................................ 422/55-58, 422/61; 436/165, 166, 169, 174, 177, 178, 524, 528, 531, 501

[56] References Cited

U.S. PATENT DOCUMENTS

| | | | |
|---|---|---|---|
| 3,689,224 | 9/1972 | Agnew et al. | 422/61 |
| 4,196,167 | 4/1980 | Olsen | 422/61 |
| 4,259,964 | 4/1981 | Levine | 422/61 |
| 4,355,113 | 10/1982 | Mennen | 422/61 |
| 4,562,043 | 12/1985 | Mennen et al. | 422/61 |
| 4,612,290 | 9/1986 | Yazawa et al. | 436/178 |
| 4,645,743 | 2/1987 | Baker et al. | 422/61 |
| 4,789,629 | 12/1988 | Baker et al. | 422/61 |
| 4,826,759 | 5/1989 | Guire et al. | 422/61 |
| 4,963,325 | 10/1990 | Lennon et al. | 422/61 |

Primary Examiner—Robert J. Warden
Assistant Examiner—Timothy M. McMahan
Attorney, Agent, or Firm—Roylance, Abrams, Berdo & Goodman

[57] ABSTRACT

A device and method for a self contained solid phase immunodiffusion assay. The device is comprised of a sample collector, and a pre-fabricated laminate which can be used in many different forms. For example, the same collector and laminate can be used with a tube having compartmentalized reagents. The seals can be broken through pressure on the sample collector. The sample collector is pushed through the seals, mixed with reagent, and then pushed into a ligand receptor reaction area which is part of the laminate. The tip of the sample collector contacts diffusable or porous membranes or filters and transfers the reactants to a capture membrane wherein a ligand receptor reaction can be examined by the naked eye or otherwise.

21 Claims, 2 Drawing Sheets

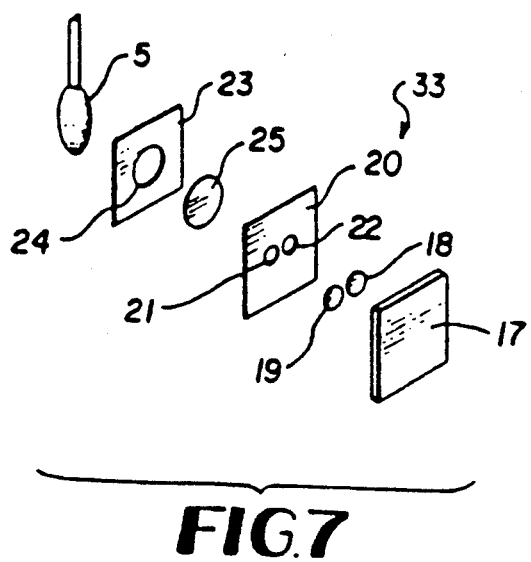
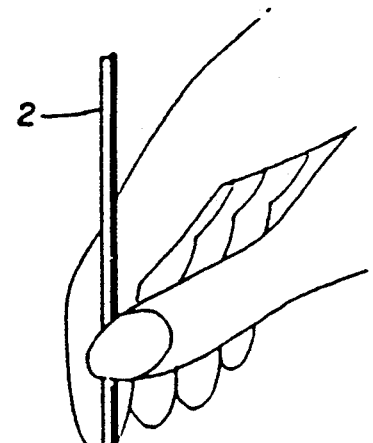
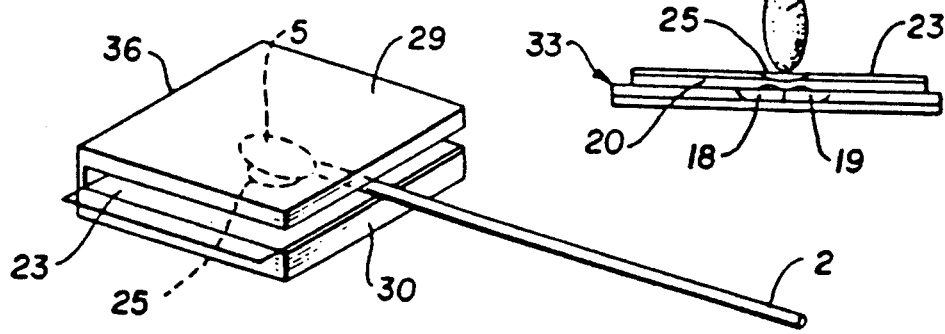
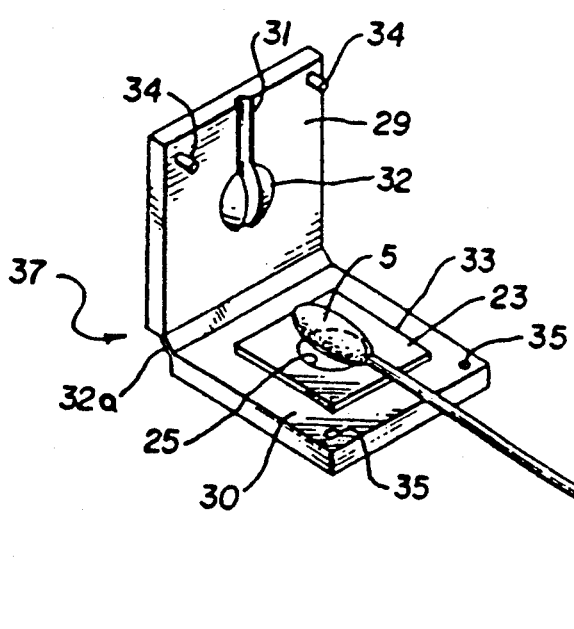

DEVICE AND METHOD FOR SELF CONTAINED SOLID PHASE IMMUNODIFFUSION ASSAY

CROSS-REFERENCE TO RELATED APPLICATION

This application is a continuation of U.S. patent application Ser. No. 07/262,503 filed as PCT/US87/03169, Dec. 1, 1987 (now abandoned); and that application Ser. No. 07/262,503 is a continuation-in-part of U.S. patent application Ser. No. 06/938,003 filed Dec. 3, 1986 now U.S. Pat. No. 4,770,853; all of the entire disclosures of which are hereby incorporated by reference as if here set forth in full.

BACKGROUND OF THE INVENTION

In order to determine the condition of a patient, and to minimize the diseased state, the need for a rapid diagnosis and appropriate treatment by health care professionals is apparent. Diagnosis of many conditions can be facilitated through the determination or quantitation of antibodies, antigens, nucleotide fragments, and other analytes from a biological specimen, which are indicative of a particular disease state or condition. A rapid, sensitive, specific, and simplistic assay is extremely useful for emergency situations, field testing, physicians' offices and in home diagnostics. As diagnostic tests become more simple and easier to perform, they are being performed away from the professional clinical laboratory setting to physicians' offices and even to the home, where untrained or poorly trained individuals perform the tests, usually following product insert instructions alone. These assays are useful, provided they are performed properly and are safe to handle for the user. Assays that require multiple steps, have multiple reagents, and have limited storage conditions are prone to misuse, especially if they are performed by individuals without adequate training or skills.

Many types of ligand receptor assays have been developed and commercialized. These assays are less expensive if capital equipment can be eliminated, such as scintillation counters, fluorometers, and colorimeters in the case of radioimmunoassay, fluorescent immunoassay, and enzyme immunoassay respectively. Non instrumental assays, such as latex agglutination, enzyme immunoassays on strips, tubes, membrane or filters have increased the usefulness and ease of performance of immunodiagnostic testing, but are still cumbersome requiring washing steps, multiple reagent additions and usually refrigerated storage conditions.

In some assays amplification or growth of viruses and bacteria are desirable before testing to increase the sensitivity of detection. In other assays adsorption steps to remove interferring substances or inhibitors of the ligand receptor assay, or long incubation of reagents are necessary to perform an assay. Each step for an assay increases the difficulty of testing for the minimally trained individual and any device that would reduce user error would improve diagnostic testing.

Horrisberger et al (J. Histo Cytochem volume 25: 295-305, 1977) described the use of colloidal gold particles in an immunoassay. Leuvering in U.S. Pat. No. 4,313,734 also describes such an immunoassay. Cerny in PCT/US patent application number 85/02534 describes a solid phase diffusion assay using gold sol particles as an immunolabel which can be visualized by the naked eye on a capture membrane, and requires no washing step. Bernstein et al (86th annual American Society for Microbiology Meeting, 1986) presented and described a rapid immunodiffusion enzyme labeled antibody assay for Group A streptococci on a membrane in which there is no washing step. Gould and Zuk in U.S. Pat. No. 4,552,839 describe the use of colored or dyed beads in a solid phase immunoassay. Through the introduction of colored immunolabelled binding reagents (i.e. gold sol particles, dyed particles, dye encapsulated liposomes, etc.) and the removal of washing steps it becomes possible to perform receptor ligand assays in a closed system with the sequential additions of all reagents within that system.

A number of antigens of interest in the diagnosis of infectious disease are collected with a sterile swab on a shaft to remove the organisms from the suspected infected area or test site (wounds, lesions, blood, tissues, pus, fluids, etc.). The swab is generally used to transfer organisms to a suitable media for culturing which may take as long as 48 hours for growth of bacteria, and 2 weeks for viruses. If the organisms are viable and do grow, then their identification could be made by biochemical, morphological or immunological methods. This time consuming method is slowly becoming replaced by more rapid immunological testing methods or DNA probe methodologies.

In many immunoassays that utilize a swab for collection of antigens or cells, the swab is placed in a solution to release the antigenic materials or cells after collection. It may be necessary to use enzymes, acids, detergents, etc. to solubilize or breakdown the antigens to expose antigenic determinants. The extracted material can then be used in an immunoassay by removing the fluid from the swab and mixing it with other reagents or adding the other reagents directly to the swab extract. In the case where membrane or filters are used to capture the immunoreactants, it is necessary to bring the fluid containing the immunoreactants in contact with the filter or membrane.

In addition, where extraneous cells or debris may interfere with an assay, it may be necessary to have a prefilter (larger pore size filter or membrane) present between the swab and the capture membrane or capture filter to retain these unwanted components.

In some assays, where antigen expression may be low, amplification can be achieved if the organisms are first cultured and then tested. If the culturing and the testing could be performed in a single device, then testing would be simplified. In some assays where there are inhibitors, cross reactive products, or clotting factors, red blood cells, etc., it may be necessary to add adsorbant materials (i.e. beads, kaolin, antibody coated particles, antigen coated particles, or lectin coated particles), anticoagulants, or buffers etc. before the ligand receptor assay can be performed.

BRIEF DESCRIPTION OF THE INVENTION

It is an object of the present invention, in one preferred form, to provide a novel test device that utilizes a swab or swab-like material (a shaft with a porous or fibrous absorbant material at one end) to collect a sample and to be able to react the sample on the swab with all the necessary reagents which are included within the device, and then to use the swab to transfer the reactants sequentially to other reactants if necessary, and finally to a reaction zone where the specific labelled reactant can be captured and visualized.

It is another object of the present invention, in a second preferred form, to provide a prefabricated assay device in the form of a laminate. This laminate, in cooperation with a swab or other sample collector device, provides a means for performing many types of ligand receptor assays. The laminate can be used in many different assay formats.

It is a further object of the present invention to provide a test device useful in performing ligand receptor assays to detect antigens, haptens, antibodies, DNA or RNA fragments, and the like, wherein the user is not required to dispense any of the reagents.

It is a particular object of the present invention to provide a test device that can be stored at nonrefrigerated temperatures, and can be utilized to perform an assay on a biological specimen or fluid without any additional reagents having to be provided to the test device.

In addition it is a further object of the present invention to provide a test device which can utilize lyophilized reagents that can be reconstituted in situ within the device.

The present invention maximizes the safety and ease of performance of ligand receptor assays through the use of apparatus designed to enable a biological specimen to be obtained by a collection device comprising a shaft and an attached tip of adsorbent or absorbent porous or fibrous material (i.e. rayon, dacron, cotton swab). In the first form of the invention, the tip is inserted into a cylindrical tube. The cylindrical tube contains a sealed vessel, or chamber, or plurality of sealed vessels or chambers in sequential order. The seal will break away or collapse when pressure of the collection device (swab) is exerted on the seal by physically pushing the collection device into and through each vessel. These sealed vessels may contain media, extraction reagents, diluents, labelled antibodies, labelled antigens, labelled lectins, anticoagulants, adsorbants, inactivators, etc. which mix with the biological specimen collected on the collection device. The reagents in these vessels may be lyophilized, enabling long term storage at non refrigerated temperature. The vessels are fixed in position in the cylindrical tube to enable the seals to be broken when physical pressure is exerted on the shaft of the collection device. The collection device holder has appropriate stop points to allow for the collection device tip to enter the appropriate vessel and mix with its contents. A key feature of the vessels are that the tip and shaft of the collection device can pass through each of the vessels into a lower portion of the cylindrical tube and attached lower portion comprising a ligand receptor reaction area. This ligand receptor area is part of a pre-fabricated laminated assay device.

The ligand receptor area is comprised of a capture membrane or a filter that will allow unbound reactants to pass through by diffusion and retain the appropriate labelled members of the binding pair. The capturing membrane or filter may be coated with a member of the binding pair to capture the reactants. If capture particles are used, then the capture filter is utilized to retain the particles and allow unbound free labelled antigen or antibody to diffuse through. A prefilter may be used between the collector tip and the capture or filter to remove any nonspecific binding due to debris. An additional absorbant material can be placed behind the capture membrane to increase the uptake of fluid. In either case a specific volume of reactants can be absorbed by controlling the size of the filter and absorbant materials.

The configuration of the lower portion allows the collection device to come into physical contact with the prefilter, capture membrane or capture filter. The prefabricated assay device is comprised of sequential layers of at least one porous membrane, an impervious shield having at least one opening, and a filter means.

BRIEF DESCRIPTION OF THE DRAWINGS

FIG. 7 is an exploded perspective view of the pre-fabricated assay device according to a second form of the invention;

FIG. 8 is a elevational view of the sample collection device in contact with the pre-fabricated assay device of the second form of the invention;

FIG. 9 is a perspective view of a prefabricated assay device and sample collection device being sandwiched between an upper hydrophobic pressure plate 29 and a lower flat hydrophobic plate 30 according to a third form of the invention; and FIG. 10 is perspective view of a prefabricated assay device showing a modification of the third form of the invention having a sample collection device positioned on a lower flat hydrophobic plate 30 which is hinged to a hydrophobic upper pressure plate 29.

DESCRIPTION OF THE PREFERRED EMBODIMENTS

In the following description, the various forms of the apparatus and the method of the invention will be described in exemplary terms only, for an antigen determining an immunoassay test. This discussion, however, is simply to illustrate the structure and use of the apparatus and the technique and steps of the method. The various forms of the apparatus clearly can be used for any ligand receptor assay in which washing steps have been eliminated and transfer of the reactants to or through a porous membrane or filter is used. The best modes, as described hereinafter, are accordingly, to be considered exemplary and not limiting as to the scope and concept of the invention.

Figure 1:
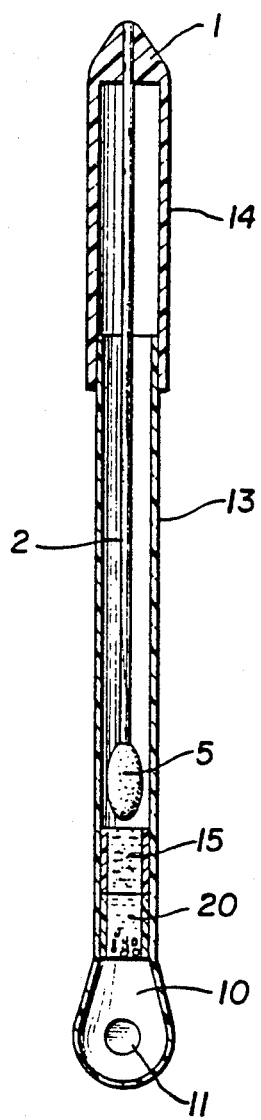
FIG. 1 is a cross-sectional view of a first form of the invention showing the collection device holder, the collection device, the tube, the sealed reagent compartments and the lower ligand receptor transfer area.

Referring first to FIG. 1 for a general depiction of the apparatus, the inventive apparatus comprises a collection device holder 14 which is comprised of a restrictive portion 1 that hold the shaft of the collection device 2 in place, a cylindrical tube 13 which is comprised of one or more sealed reagent compartments 15 and 20, and a lower ligand receptor reaction area 10. Area 10 is drawn enlarged, but can be smaller, see FIG. 5 for example.

Figure 2:
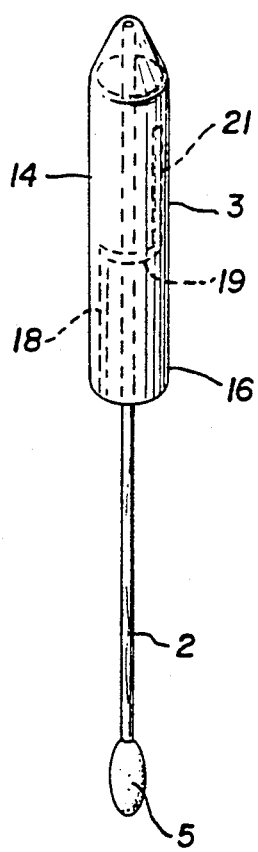
FIG. 2 is a perspective view of the basic structure of the collection device holder and collection device of FIG. 1 including the grooves for guiding the movement of the collection device through the apparatus.

Referring to FIG. 2, the collection device holder 14 has a nodule 16 which positions onto the cylindrical tube and prevents the apparatus from being accidentally opened. Nodule 16 can be heat sealed or made to cooperate with a groove formed in tube 13, or the cooperating nodule 17 shown in FIG. 3 or other means can be provided to accomplish the sealing function. When a sample is to be taken, the collection device holder is removed and separated from the cylindrical tube by twisting and pulling up on the collection device holder. This frees up the collection device holder which is then used to collect the test sample (i.e. throat swab, pus, blood, urethral swab, etc.) by allowing the collection device tip 5 to come into contact with the suspect tissue, fluid, wound, etc.

Figure 3:
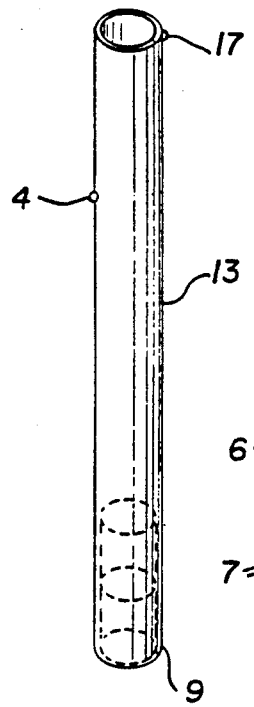
FIG. 3 is a perspective view of the basic structure of the tube of FIG. 1, its compartmentalized reagents, and the nodule which fits into the groove of the collection device holder.
Figure 4:
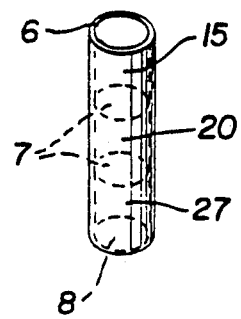
FIG. 4 is a perspective view of the sealed compartments (i.e. vessels) of the apparatus of FIG. 1.

Referring to FIG. 2 and FIG. 3, after obtaining a test sample, the collection device holder is replaced onto the cylindrical tube 13 and turned until the nodule 4 (FIG. 3) on the cylindrical tube is in alignment with the groove 18. The collection device holder is then manually forced downward until the nodule 4 stops at the horizontal groove 19. When the nodule 4 is in contact with horizontal groove 19, then simultaneously the tip 5 will have broken through the first seal (FIG. 4), mixing with the contents of the first chamber 15, then breaking through seal 7 and emptying its contents into chamber 20. The number of independent chambers is related to the number of required reagent additions and incubation steps. One chamber or a plurality of chambers could be used and the mixing of reagents controlled using the principles of nodule 4 and grooves 18, 19 as previously described. In the preferred embodiment, the collection device holder is turned to the right and then back and forth using groove 19 to mix the contents of vessel 20 through the simultaneous turning of the collection device tip.

Referring to FIGS. 2 and 3, after an appropriate incubation time, the collection device holder 14 is turned to the right and thus aligning nodule 4 (FIG. 3) with groove 3 (FIG. 2) and then manually forced downward until the movement of nodule 4 is stopped by the groove end 21 (FIG. 2).

Figure 5:
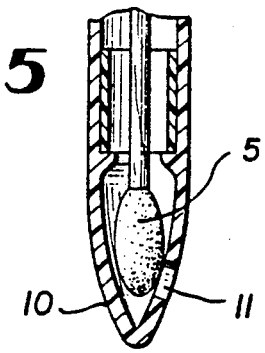
FIG. 5 is a cross-sectional side view of the lower portion of the apparatus of FIG. 1 showing the final position of the collection device tip at the window of the ligand receptor area.
Figure 6:
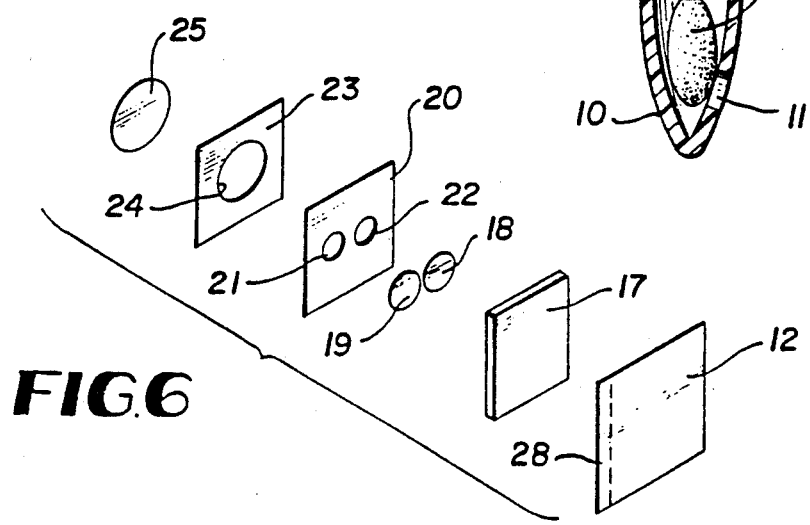
FIG. 6 is an exploded perspective view of the ligand receptor test area as used in the apparatus in FIG. 1.

Referring to FIGS. 5 and 6 the lower portion 10 may be physically one piece with the cylindrical tube 13 or may be an attached separate piece. When the nodule 4 is in contact with the groove end 21, then the collection device tip 5 is in contact with the prefilter membrane 25 through the window 11. The reactants flow through the prefilter membrane through holes 24 of impervious shield 23 which holds the prefilter membrane 25 against hole or window 11. The shape of the lower portion 10 is configured to enhance contact of the collection device tip 5 with the prefilter or reaction membranes. If preferred, the prefilter could be placed on the inside wall of the window 11. In any case, the reactants flow through holes 21 and 22 of shield 20 which holds membranes 18 and 19 respectively in place. The holes 21 and 22 restrict the flow of the reactants through a capture membrane 19 and a control membrane 18 and enhance the signal of the reaction by concentrating the labelled ligand or receptor binding pairs into a small area. Absorbant 17 absorbs excess fluid diffusing through the membranes. When an appropriate volume of fluid has diffused through the membranes, usually by saturation of the absorbant, the capture and control membrane are examined within the holes 21 and 22 respectively by lifting the tab 28 of the adhesive tape 12.

In the preferred form of the invention, the assay results are examined by the naked eye since color changes are the result. However the invention is not limited in this manner and the "examination" of test results could be done with instruments or otherwise dependent upon the protocol of the particular assay.

Adhesive tape 12 holds the absorbant 17 in place and applies the necessary pressure to insure diffusion of fluid through the various layers of the ligand receptor test device 33A. The color intensity of the capture membrane 18 is compared to the color intensity of the control membrane 19. A positive result is determined by viewing a more intense color in the capture membrane than in the control membrane. A negative result is determined by no significant color or the same weak color in the capture and control membranes. In competitive inhibition assays the positive and negative results are reversed. In the performance of drug analyte assays, the size of the ring of color in a single larger capture membrane is related to the concentration of drug in the test sample. The design of the ligand receptor area, the coating of reagents on the membranes, and the addition or deletion of capture or control membranes are dependent on the particular type of assay being performed. The capture membrane can be coated with antigen or antibody, or other complementary ligands or receptors and can be used to determine the presence of different antigens or antibodies. The number of chambers used in the apparatus is dependent upon the type of assay and can contain diluents, media for growth amplification of microorganisms, lyophilized labelled ligands or receptors, etc. The seal 7 (FIG. 4) may be attached to two chambers simultaneously or may be independent. Therefore the chambers could be attached to each other or be independent.

Referring to FIG. 6, the prefilter 25 is fixed around the periphery of hole 11 in tube 10 by taping, gluing, heat sealing, chemically sealing, sonic welding, or the like. Impervious shield 23 is a single side adhesive coated laminate having adhesive on the side facing the prefilter 25. The impervious shield laminate 23 with hole 24 fixes and exposes the prefilter to the tube 10 and hole 11. The impervious shield 20 can also be a single side adhesive coated laminate which fixes membranes 18 and 19 onto absorbent 17. Absorbent 17 is fixed on the side opposite to the positioned membranes with adhesive tape 12. The adhesive tape 12 fixes the assay device 33A to tube 10. Alternative means of fixing can include clamps, glues, or the like. In order to examine a test result on the membranes 18 and 19 it is necessary to separate the impervious shields 23 and 20 from each other to expose the membranes. By pulling back adhesive tape 12, a portion of the assay device 33A consisting of shield 20, membranes 18 and 19, and absorbent 17 separates from filter 25 and shield 23, thereby exposing membranes 18 and 19 for examination.

Referring to FIG. 7, the pre-fabricated assay device 33 is a laminate comprised of a prefilter membrane 25 held in place by a hydrophobic impervious shield 23 having a hole 24 through which reactants from absorbent tip 5 can flow into the prefilter. When absorbent tip 5 is pressed into contact with prefilter 25, the flexible prefilter is forced into contact through holes 21 and 22 selectively clustered and sized in impervious shield 20 with control and capture membranes 18 and 19. The fluid reactants from tip 5 flow from prefilter 25 to both membranes 18 and 19 simultaneously. Absorbent 17 is in contact with membranes 18 and 19 and the fluid reactants diffuse through membranes 18 and 19 to absorbent 17. At the conclusion of a ligand receptor assay the impervious shield 23 with attached prefilter 25 is removed and membranes 18 and 19 are examined by the naked eye, or otherwise, for any color change, or the like.

FIG. 8 is a perspective view of a collection device tip 5 being manually brought into contact with an assembled pre-fabricated assay device 33. The fluid of a labelled ligand or receptor reagent in combination with sample is transferred from tip 5 through prefilter membrane 25 and through control and capture membranes 18 and 19 to absorbent 17. This shows the general utility of the invention devices 33 and 33A to be used in many different environments.

FIG. 9 is a perspective view of a sandwich device 36 for holding collection device tip 5 under pressure against a pre-fabricated assay device 33. Hydrophobic upper pressure plate 29 is movable and hinged to hydrophobic lower flat plate 30. After reacting sample collection device tip 5 with labelled ligand or labelled receptor by manipulating shaft 2, the sample collection device tip 5 is positioned horizontally in contact with prefilter membrane 25 and pressure is applied to the device forcing the absorbent tip 5 to push the prefilter 25 into contact with porous membranes 18 and 19 and allowing the reactants to flow through and into the pre-fabricated assay device 33. Pressure can be applied to pressure plate 29 by means of a weight, clamp, manually squeezing, or the like. After an appropriate period of time to allow the fluid reactants to penetrate the assay device 33, pressure is removed from the hinged sandwich device and the impervious shield 23 is lifted to allow the control and capture membranes of the pre-fabricated assay device to be examined.

FIG. 10 is a perspective view of a hinged sandwich device 37 for applying pressure to sample collection device tip 5 and the pre-fabricated assay device 33. Upper hydrophobic pressure plate 29 is contoured as at 31 to the sample collection device 2 and 5 to maximize the amount of fluid that can flow into the pre-fabricated assay device 33 which is positioned on the lower hydrophobic plate 30. Upper plate 29 is formed with a groove 31 to accept shaft 2 of the collection device, and with a composite male and female protrusion 32 contoured to accommodate shaft 2 while permitting the application of pressure to squeeze tip 5. After the sample collection device has reacted with labelled ligand or labelled receptor the sample collection device is manually placed within the hinged sandwich device 37 with sample collection device tip 5 in contact with prefilter membrane 25 and pressure is applied to and maintained by the hinged sandwich device 37. The hinged sandwich device 37 consists of a hinge 32a and a clamping mechanism such as protrusions 34 from upper pressure plate 29 and a complementary fitted piece such as the orifices 35 which will produce a friction fit and maintain the closed clamped position of the hinged sandwich device 37. After an appropriate time period the hinged sandwich device is opened and the prefilter membrane 25 is removed to expose the control and capture membranes of the pre-fabricated assay device 33.

In FIGS. 9 and 10, the assay device 33 can be layed loosely, or affixed as by glueing or the like to one of the plates 29 or 30. Also a form fitted depression to hold the device 33 could be formed in a plate 29 or 30.

DEFINITIONS

In the following section certain terms used in the specification and claims herein shall be understood to have the following meanings:

Ligand: Any organic compound for which a receptor naturally exists or can be prepared including haptens, antigens, sugars, vitamins, peptides and the like.

Receptor: Any compound capable of recognizing a specific molecular configuration of a ligand including antibodies, lectins, enzymes, nucleic acids, Fab fragments, avidin and the like.

Ligand receptor reaction: Any binding between a receptor and its complementary ligand.

Porous membrane: any porous solid matrix including porous spreding layers, bibulous papers, filters, and the like.

Coated porous membrane: A porous membrane that has a ligand or receptor covalently or noncovalently attached to its surface.

Impervious shield: any hydrophobic material that will not allow diffusion of fluid to occur through its surface. This material can be plastic, a plastic adhesive laminate, and the like.

Chamber: a partitioned space, vessel, reservoir, compartment or the like.

The following example is illustrative:

EXAMPLE 1

A Rapid Immunodiagnostic Test for Group a Streptococci

Group C phage associated lysin enzyme which is effective in fragmenting and solubilizing the Group A streptococcal polysaccharide was diluted in a buffer of .05M citrate phosphate pH 6.1 containing 0.005 EDTA, 0.005 DTT, 0.1% rabbit IgG, 0.05% sodium azide and mixed with rabbit anti streptococcal Group A coated gold sol particles ($OD^{518}$ 1.5) diluted in a buffer of 0.02 Tris pH 8.2 containing 1.0% BSA, 0.2% sodium heparin, 0.5% n-acetylglucosamine and 0.02% sodium azide in a ratio of 3 parts lysin reagent to 1 part antibody gold sol reagent. The combined reagent was sterile filtered through a 0.2 micron cellulose acetate filter and 200 microliters were aliquoted into acrylic walled reaction cup vessels, having an aluminum foil sealed bottom. The aliquots were frozen and lyophilized. The reaction cup vessels were sealed with aluminum foil and contact cement under nitrogen. Another reaction vessel was cemented to the aluminum foil lid of the first vessel. Two hundred microliters of distilled water was added to the second vessel and then cemented and sealed with aluminum foil. The vessels were placed and positioned into the cylindrical tube. The ligand receptor area was prepared by coating nitrocellulose membranes with rabbit anti Group A streptococcal antibody for the capture membranes, and normal rabbit immunoglobulin for the control membrane. The membranes were dried and fixed to a diacetate laminate which had 1.5 mm diameter holes for each membrane. A 1.2 micron cellulose acetate prefilter was used to cover the hole (window) in the lower portion of the tube. A dacron tipped swab was seeded with varying concentrations of group A streptococci. The swab was placed into the cylindrical tube and forced downward to break the first two seals on the reaction vessels. The swab was incubated for 4 minutes at room temperature allowing the lysin enzyme to solubilize the Group A streptococcal polysaccharide and the reaction of the gold labelled anti Group A antibody to form complexes with the released polysaccharide. After the four minutes, the swab was forced downward through the third seal into the lower portion, coming in contact with the ligand receptor area 33. The fluid diffused through the prefilter into the capture and control membranes. After 30 seconds the tab 28 on the ligand receptor area 33 was pulled away from the lower portion and examined by eye. A distinct color reaction with $2 \times 10^3$ organisms of Group A streptococci could be distinguished in the capture membrane compared to the colorless control membrane.

The foregoing disclosure and the showing made in the drawings are merely illustrative of the principles of this invention and are not to be interpreted in a limiting sense. It is to be understood that, through the example and embodiments described herein, various modifications in light thereof will be suggested to persons skilled in the art. Thus, it is to be understood that the protection granted is to be limited only within the spirit of the invention and the scope of the following claims.

I claim:

1. A method of performing a ligand receptor assay in an assay test device wherein a ligand receptor complex is captured on at least one porous capture membrane in the test device, comprising the steps of providing sample collector means, collecting a specimen with said sample collector means and contacting the specimen with one or more reactants as required to perform said assay; providing at least one porous membrane located in the test device as required to perform said assay to capture any ligand receptor complex formed as a result of the performance of this and the preceding steps; causing liquid diffusion in the assay test device from the specimen and the reactants on said sample collector means to all of said at least one porous membrane simultaneously to capture said ligand receptor complex while the membrane is a part of the test device; and examining all of said at least one porous membrane after performance of all of the preceding steps while said at least one porous membrane is a part of the test device; whereby any change caused by a labelled ligand or a labelled receptor being captured or not being captured on said at least one membrane in accordance with the protocol of said assay can be readily observed.

2. The method of claim 1, and the additional steps of providing two of said porous membranes, and causing the other of said two porous membranes to be a control membrane.

3. The method of claim 1, and the additional step of filtering said specimens and reactants during said liquid diffusion step using filter means having a pore size selected to be large enough to permit said liquid diffusion step and small enough to prevent debris larger than said selected pore size which may be on said sample collector means from contacting any of said at least one porous membrane.

4. The method of claim 1, and performing said liquid diffusion step by including the sub-step of creating physical pressure at least indirectly between said sample collector means and all of said at least one porous membrane simultaneously.

5. The method of claim 1, and performing the method using a pre-fabricated assay device, and constructing said assay device comprising the following steps and providing sequential layers as follows:
   (a) said at least one porous membrane;
   b) impervious shield means;
   c) forming at least one opening in said impervious shield means equal in number to the number of said at least one porous membrane and sizing and clustering said at least one opening so that said liquid diffusion can be performed through all of said at least one opening simultaneously;
   d) filter means; and
   e) selecting a pore size for said filter means large enough to permit said liquid diffusion and small enough to prevent debris larger than said selected pore size which may be on the sample collector means from contacting any of said at least one porous membrane.

6. The method of claim 5, and the additional steps performed during said construction of said pre-fabricated assay device of providing an absorbent means layer, and locating said absorbent means layer next to said at least one porous membrane on the side thereof opposite said impervious shield means.

7. A pre-fabricated ligand receptor assay device comprising sequential layers of:
   a) at least one porous membrane adapted to capture any ligand receptor complex formed during the use of said assay device,
   b)
      i) impervious shield means formed with at least one opening equal in number to the number of said at least one porous membrane,
      ii) means for sizing and clustering said at least one opening so that liquid diffusion between said at least one porous membrane and a reactant brought into contact with said assay device can occur through all of said at least one opening simultaneously,
   c) filter means having a pore size large enough to permit said liquid diffusion and small enough to prevent debris larger than said selected pore size from contacting any of said at least one porous membrane,
   a sample collection means comprising an elongated shaft and an absorbent tip, and a sandwich device, said sandwich device comprising a pair of plate means, means to hinge said plate means together along one respective side of said pair of plate means, positioning said pre-fabricated assay device between said plate means, and means to apply pressure to said tip when said tip is inserted between said pair of plate means and in contact with said pre-fabricated assay device.

8. The device of claim 7, and means to apply pressure to said tip when said tip is in contact with said assay device, and said means to apply pressure comprising contoured protrusion means adapted to bear on said tip.

9. A kit containing the device of claim 7, said kit including a container containing liquid labelled receptor or labelled ligand reagent for cooperation with said sample collection means and selected in accordance with the protocol of said assay.

10. The device of claim 9, wherein said labelled reagent comprises a chromophore.

11. The device of claim 10, wherein said chromophore comprises a dye.

12. The device of claim 10, wherein said chromophore comprises a dyed particle.

13. The device of claim 10, wherein said chromophore comprises a pigment.

14. The device of claim 10, wherein said chromophore comprises a metal sol particle.

15. The device of claim 10, wherein said chromophore comprises a dye encapsulated liposome.

16. The device of claim 7, and said pre-fabricated assay device including an absorbent layer in contact with said at least one porous membrane on the side thereof opposite said impervious shield.

17. The device in claim 7, said means to apply pressure comprising clamping means.

18. The device of claim 7, and a second porous membrane, said second porous membrane comprising a control membrane.

19. The device of claim 7, and said assay device including an absorbent layer in contact with said at least one porous membrane on the side thereof opposite said impervious shield.

20. The device of claim 19, wherein at least said impervious shield, said at least one membrane and said absorbent layer are prefabricated in the form of a laminate.

21. The device of claim 7, and said means to apply pressure comprising contoured protrusion means adapted to bear on said tip.

* * * * *